June 1, 1965 W. E. LAMMERTS Plant Pat. 2,526
ROSE PLANT
Filed Jan. 15, 1964
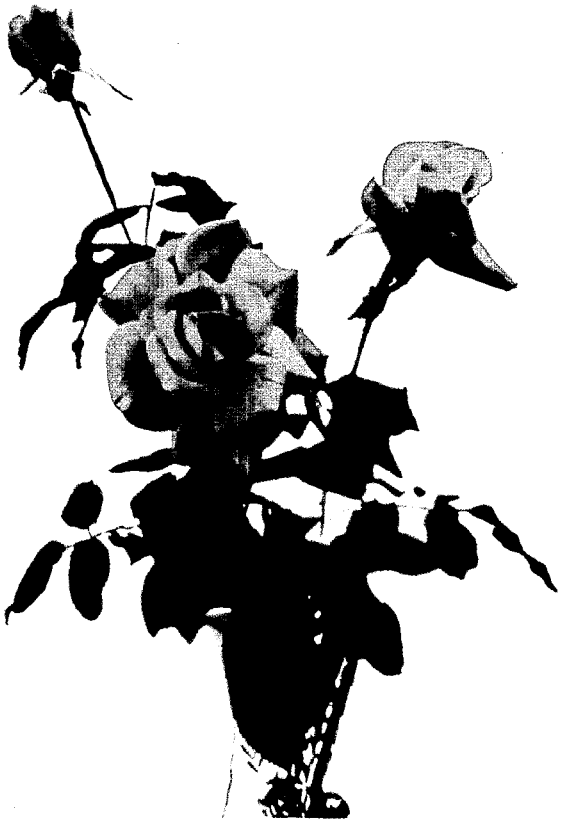
INVENTOR:
WALTER E. LAMMERTS
BY: Rummler & Snow
ATT'YS United States Patent Office Plant Pat. 2,526
Patented June 1, 1965

2,526
ROSE PLANT

Walter Edward Lammerts, Livermore, Calif., assignor to Amling-Devor Nurseries, Inc., Livermore, Calif., a corporation of California Filed Jan. 15, 1964, Ser. No. 337,965
1 Claim. (Cl. Plt.—20)

This invention concerns a new and distinct variety of grandiflora rose plant which I developed in the course of breeding efforts carried on by me, in nursery grounds at Livermore, California, with the object of producing a rose combining the bright red color of "Merry Widow" (Plant Pat. 1,711) with the grandiflora habit and vigor of "Queen Elizabeth" (Plant Pat. 1,259) in a hybrid plant having good bud and open flower form.

This new variety of rose plant originated as a seedling produced by crossing "Queen Elizabeth," as the seed parent, with "Merry Widow," as the pollen parent, and was observed to have blooms of a remarkably uniform and distinctive color, quite different from presently known commercial varieties. The flower is of a luminescent rose red color with an undertone of geranium red reminiscent of "Grande Duchesse Charlotte" (Plant Pat. 774), the pollen parent of "Merry Widow." The flower of this new variety is thus distinctive in color from the dark chrysanthemum crimson "Merry Widow" as well as from the geranium red "Grande Duchesse Charlotte." The novel color of the new variety was also observed to be unusually long lasting, with a very slow fading reaction, so that very little color change occurs before petals drop and, because this plant has genetic factors for the recessive undertone of geranium lake, the blooms avoid the usual "blueing" of many red roses.

These and other advantages hereinafter described, as well as the accomplishment of the before-mentioned objectives led to asexual propagation of this new variety of rose plant, under my direction at Livermore, California, for further study of its commercial possibilities and successive propagations, by budding, have demonstrated that the novel characteristics and advantages of the new variety are consistent and firmly fixed.

My new variety of rose plant is illustrated in the accomapnying full color drawing which shows the nature of the foliage as well as the form of the bud and the fully opened blooms; and the following is a detailed description of the new variety with color designations according to the Horticultural Color Chart of the British Colour Council.

*The plant*

Origin: Seedling.
Parentage:
*Seed parent.*—"Queen Elizabeth" (P.P. 1,259).
*Pollen parent.*—"Merry Widow" (P.P. 1,711).
Classification:
*Botanic.*—Rosa hybrida.
*Commercial.*—Grandiflora.
Form: Bush.
Height: 5 to 6 feet.
Growth: Tall, compact, and very vigorous.
Strength: Strong and with rapid new cane growth.
Branching: Upright and well branched.
Foliage:
*Quantity.*—Abundant, well clothed.
*Size of leaf.*—Large, 4 to 5 inches wide and 6 to 7½ inches long.
*Size of leaflet.*—Lateral ⅞ to 1⅜ inches wide and 1¾ to 2¾ inches long. Terminal—1¼ to 2½ inches wide and 2½ to 3½ inches long.
*Shape of leaflet.*—Elongate and finely serrated.
*Texture.*—Leathery, smooth, and glossy.

*Color.*—Upper side—Spinach Green (0960). Under side—Spinach Green (0960/2).
*Petioles.*—1 to 1½ inches long.
*Ribs and veins.*—Not strongly indented on upper surface or obtruding on under side.
*Rachis.*—Have 2 to 4 very small thorns on underside.
Plant has thorns and prickles. Size of thorns: ½ to ⅝ inch long and ⅛ to 3/16 inch wide at base; ⅜ to ½ inch high and downwardly curved.

*Bud*

Form: Medium long and pointed. Open slowly.
Size: 1⅜ to 1¾ inches long and 1 to 1¼ inches wide. At ¼ open stage: diameter, about 1½ to 1¾ inches; depth, 1½ to 1¾ inches.
Color: When sepals first divide—Chrysanthemum Crimson (824). When petals begin to unfurl—Currant Red (821).
Sepals: Spear shaped. Upstanding and clasping over bud at first. As bud opens—⅛ to ¼ open stage—the sepals curl back. Alternate sepals have 2 small lance-shaped appendages each ¼ inch long. Color: inside—Willow Green (000862/2); outside—Scheeles Green (860/1).
Calyx: Long and funnel shaped. Does not split and is of a generally smooth aspect with very few, gland tipped, small hairs.
Peduncle: Slender and erect. Smooth and shiny and 1½ to 2 inches long. Color—Scheeles Green (860/1).

*Flower*

Blooms: Continuously and profusely, from early spring through late fall.
Size: Medium. Diameter—4 to 4½ inches. Depth—2 inches.
Borne: Singly and in clusters of 3 to 5 flowers. The stems of the flowers in clusters are usually long enough for cutting, i.e. 6 inches or more in length.
Peduncle: Sturdy and upright.
*Length.*—2 to 3 inches.
*Color.*—Fern Green (0862)
Shape: High center when bloom first opens. Changing later to a flat form, but with the under petals tending to cover the anthers and pistils in the flower center.
Petalage: 20 to 25 petals, loosely but regularly imbricate in arrangement.
*Form.*—Obovate and smooth. 1⅝ to 1¾ inches wide and 1⅞ to 2 inches long, narrowing gradually to a width of about ½ inch at the base.
*Color.*—Outer petals—Rose Red (724) with an undertone of Geranium Lake (20). Petal base—Rose Red (724) with a ⅛ inch arc of light Canary Yellow (2/3). Inner petals and the reverse side of all petals have the same color as the outer petals.
Petals stay for 4 to 6 days.
Petaloids:
*Number.*—3 to 5.
*Size.*—¾ to 1½ inches long. ¼ to ¾ inch wide.
*Color.*—Same as petals—Rose Red (724).
Texture: Soft. Appearance—satiny.
Discoloration: Very slight, after full bloom.
Effect of weather: Not adversely affected by wet weather. In very hot weather the color is of a lighter rose red than otherwise.
Persistence: Petals drop off cleanly.
Lasting quality:
*On plant.*—4 to 6 days.
*As cut flower.*—3 to 5 days.
Fragrance: Moderate, spicy.
Disease resistance: Moderately resistant to mildew and rust as observed at Livermore, California.

*Reproductive organs*

Stamens:

*Anthers.*—135 to 155. Irregularly arranged and 1/16 to 1/8 inch long.

*Filaments.*—1/8 to 3/8 inch long.

Pistils: 65 to 80. 1/4 inch long.

Stigmas: Color—Sulphur Yellow (1/3).

Ovaries: Large, well formed, heavily clothed with silvery hairs.

*Fruit*

The fruit is fertile, round in shape, and its color at maturity is yellow tinged orange.

This variety of rose plant most nearly resembles its pollen parent "Merry Widow." It is also comparable with "Queen Elizabeth" in vigor and inherits much of the grandiflora habit of "Queen Elizabeth," i.e. its tall, compact growth and the production of flowers both singly and in clusters, with most of the flowers in clusters having stems 6 inches or more long. The flower production of the new variety, like that of "Queen Elizabeth," is abundant and continuous. The buds, however, are long pointed and distinct in shape from either "Merry Widow" or "Queen Elizabeth" in that the sepals remain clasping for a longer time as the bud enlarges, thus providing a pleasing contrast of dark green and crimson color.

As the outer petals of the bud develop and the bud elongates, they have long silvery hairs which are most unusual and give the opening bud a gossamer sheen. As the bud opens it is high centered and the open flower, though not a formal imbricate one, has a pleasing arrangement of petals in that the central one remain upright and cover the stamens and pistils. As before mentioned, the luminescent rose red color of the open bloom, with its undertone of geranium red, is long lasting with almost no color change occurring before the petals drop.

The leaves though smaller and more elongate than those of "Queen Elizabeth," have the same desirable glossy appearance and strong leathery texture as those of "Queen Elizabeth" and the green foliage abundantly clothes the flowering plant.

Having thus shown and described my new variety of rose plant, I claim:

A new and distinct variety of rose plant, substantially as herein shown and described, particularly characterized by the distinctive luminescent red rose color of its blooms which includes an undertone of geranium red, by the uniform color of the bloom which is the same throughout the petals and on both sides of the petals, by the resitsance of the bloom to fading and the very small color change before the petals drop, and by the clasping sepals on the maturing bud and the long silvery hairs which appear on the outer petals of the bud as they develop and the bud elongates.

No references cited.

ABRAHAM G. STONE, *Primary Examiner.*